United States Patent [19]
Kling

[11] Patent Number: 5,858,013
[45] Date of Patent: *Jan. 12, 1999

[54] ABSORBENT PANT DIAPER HAVING FRICTION INCREASING MEANS

[75] Inventor: Robert Kling, Skene, Sweden

[73] Assignee: Mölnlycke AB, Göteborg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 676,345

[22] PCT Filed: Feb. 17, 1995

[86] PCT No.: PCT/SE95/00169

§ 371 Date: Jul. 19, 1996

§ 102(e) Date: Jul. 19, 1996

[87] PCT Pub. No.: WO95/22306

PCT Pub. Date: Aug. 24, 1995

[30] Foreign Application Priority Data

Jan. 18, 1994 [SE] Sweden .................................. 9400569

[51] Int. Cl.⁶ .................................................. A61F 13/15
[52] U.S. Cl. .......................... 604/386; 604/392; 604/396; 604/393; 2/337
[58] Field of Search ............................ 604/385.1, 385.2, 604/386, 387, 388, 389, 390, 391, 392, 393, 394, 396; 2/337

[56] References Cited

U.S. PATENT DOCUMENTS

| | | |
|---|---|---|
| 1,817,991 | 8/1931 | Langrock .................................. 62/337 |
| 2,141,105 | 12/1938 | Eller et al. ................................ 604/394 |
| 2,633,132 | 3/1953 | Kligler et al. ........................... 604/386 |
| 3,076,201 | 2/1963 | Winter ......................................... 2/337 |
| 3,424,162 | 1/1969 | Porravicini ............................... 604/396 |
| 3,613,687 | 10/1971 | Kennedy .................................. 604/396 |
| 4,205,679 | 6/1980 | Repke et al. ......................... 604/385.2 |
| 4,834,739 | 5/1989 | Linker, III et al. . |
| 4,850,992 | 7/1989 | Amaral et al. .......................... 604/389 |
| 5,064,421 | 11/1991 | Tracy ....................................... 604/386 |
| 5,163,932 | 11/1992 | Nomura et al. ......................... 604/391 |
| 5,476,458 | 12/1995 | Glaug et al. ............................ 604/395 |

FOREIGN PATENT DOCUMENTS 9317648  9/1993  WIPO .

*Primary Examiner*—Mark O. Polutta
*Attorney, Agent, or Firm*—Burns, Doane, Swecker & Mathis, L.L.P.

[57] ABSTRACT

The present invention discloses a disposable absorbent pant or diaper having a crotch portion and front and back portions adjacent thereto which are joined to form a waist portion surrounding the waist of the user. The waist portion is circumferentially elastic around the waist of the user. At least one cover layer extends from at least the front portion to the back portion and an absorbent body is disposed adjacent to the at least one cover layer. The absorbent body is held tightly against the body of the user by the elastic waist portion. At least portions of the surface of the waist portion facing the skin of the user are provided with a friction agent to form a friction increasing surface against the skin of the user.

16 Claims, 3 Drawing Sheets

ABSORBENT PANT DIAPER HAVING FRICTION INCREASING MEANS

TECHNICAL FIELD

The present invention is directed to a disposable absorbent pant or diaper and, more particularly, to a disposable absorbent pant or diaper having a waist portion with elements for increasing the frictional resistance upon contact with the skin of the user, such that the circumferential elastic may be reduced.

BACKGROUND OF THE INVENTION

The present invention relates to a pair of absorbent pants or a pant diaper for one-time use, comprising a crotch portion, front and back portions adjacent thereto, which are joined to form a waist portion surrounding the waist of the user, said portion being circumferentially elastic, an absorbent body, which is held tightly against the body of the user by the elastic waist portion. Such an absorbent pant diaper is known by our own Swedish patent application 9200663-4, having around the waist elastically extensible elements, for example elastically extensible strings, strips, film, fibre fabric, laminates or the like, which are designed to hold the pant diaper in place on the user and prevent it from slipping down from its intended position of use. In order to prevent the elastic tension from being uncomfortable for the user, the known pant diaper is provided with a large number of elastic elements, which, by virtue of their number, on one hand exert a sufficient total tightening force around the waist of the user for the pant diaper to not slip down, and, on the other hand, each does not exert an excessive local pressure on the user. However, the use of a large number of elastic elements involves a relatively high material cost. It is therefore desirable to be able to reduce the need for elastic elements in the waist portion of the pant diaper without having to deviate from the requirement that the pant diaper should stay up comfortably on the user.

SUMMARY OF THE INVENTION

These and other problems are solved by a disposable absorbent pant diaper of the type described by way of introduction which is characterized in that at least portions of the surface of the waist portion facing the skin of the user are provided with a friction agent to form a friction increasing surface against the skin. This prevents the pant diaper from slipping down, in a very inexpensive and simple manner without having to use many elastic threads. This makes it possible to supply a very limited number of pant waist sizes while still requiring that the pant diaper should stay in place during use. The present invention can, however, also be used with advantage on a pant diaper having a large number of elastic elements in the waist portion. In this case, it is possible to reduce the tension which the elastic elements exerts on the user, since the frictional force of the friction agent compensates for the reduced friction resulting from the lowering of the elastic tension. It is of course possible to use the invention on other types of pant diapers as well, which do not use a large number of elastic elements in the waist, for the purpose of improving the friction against the body of the user, i.e. improving the stay-up capacity of the pant diaper.

U.S. Pat. No. 4,834,739 describes the use of friction coatings on a sanitary napkin to keep the napkin in place relative to the underpants and thighs of the wearer. This invention is, however, directed to an entirely different problem as is mentioned above and an entirely different field, namely a sanitary napkin which is held up by the user's underpants.

BRIEF DESCRIPTION OF THE DRAWINGS

The present invention will now be described in more detail with reference to the accompanying drawings, where.

DESCRIPTION OF THE PREFERRED EMBODIMENTS

Figure 1:
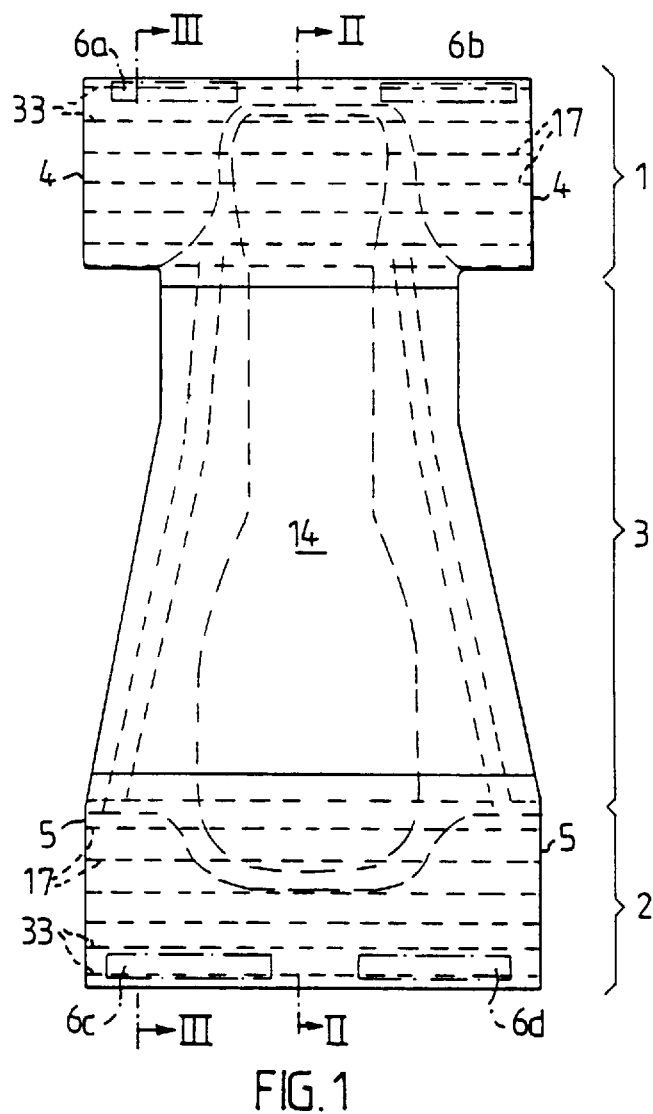
FIG. 1 shows a schematic plan view of an absorbent pant diaper according to one embodiment of the invention as seen towards the outside of the pant diaper in a state in which the front and back portions of the pant diaper have still not been joined for forming the waist opening and the leg opening, and in which the elastic elements in the pant diaper are in their stretched-out state.
Figure 2:
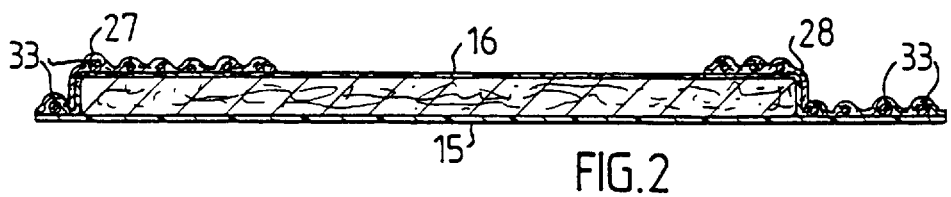
FIG. 2 shows a section along the line II—II in FIG. 1.
Figure 3:
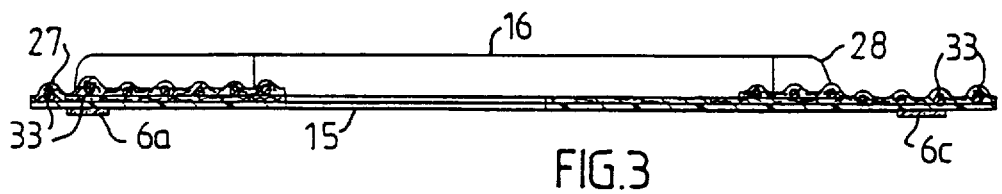
FIG. 3 shows a section along the line III—III in FIG. 1.
Figure 4:
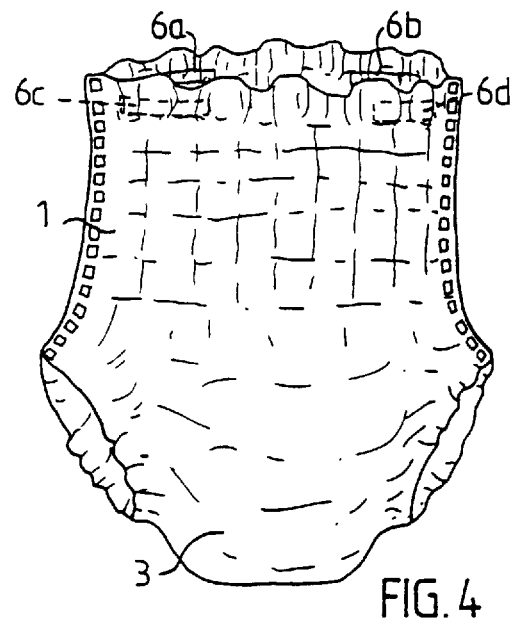
FIG. 4 shows a view from the front of the pant diaper in its assembled state.

FIG. 1 thus shows an absorbent pant diaper in its still non-assembled state, i.e. the waist and leg openings of the diaper have still not been formed. The pant diaper comprises a front portion 1, intended to be applied to the front of a user, a back portion 2, intended to be applied to the rear of the user, and a crotch portion 3 between the front and rear portions 1, 2 intended to be applied between the legs of the user. The front and back portions 1 and 2 also each have two side edges 4, 5 intended to be attached together to form a pant diaper according to FIG. 4. The pant diaper further comprises an absorbent body 14 extending in the longitudinal direction of the diaper and which is enclosed between an inner cover layer 15 and an outer cover layer 16. The inner cover layer 15 is applied on the wetting side of the absorbent body 14 facing the user. It is liquid-permeable and consists, for example, of fibre fabric, a so-called non-woven. The outer cover layer 16 is liquid-impermeable or at least hydrophobic and can, for example, consist of a layer of polyethylene or a fibre fabric which has been coated or laminated with polyolefines, for example, so that it is made liquid-impermeable or at least hydrophobic. The absorbent body 14 can, for example, comprise cellulose fibres as absorbent material. Furthermore, it can comprise other absorbent materials such as polymer hydrocolloid materials, for example in particle form.

Such materials are usually called super-absorbents defined as materials with a capacity to absorb liquid many times its own weight. A plurality of transverse elastic elements 17, for example elastic threads, tapes or the like, are applied in a pretensioned state across both the front and back portions 1, 2. The required number of such elastic threads is, however, less here than in previously known pant diapers with the same stay-up capacity.

In the front and back portions 1 and 2, respectively, layers 27 and 28, respectively, of textile-like material, for example fiber fabric, are arranged on the outermost layer of the pant diaper. The elastic threads 17 are applied between these layers 27, 28, and the outer cover layer 16 or the inner cover layer 15, respectively, within those portions of the front or back portion in which the outer cover layer 16 does not extend.

The rear layer 28, as does the front layer 27, extends somewhat in over the rear or front edge of the absorbent body, thus also covering a portion of the outer cover layer 16. Along the front and back waist portions of the pant diaper, there extend two elastic elements 33, which can consist of elastic threads, tapes or the like applied pretensioned and which in this embodiment have a greater contractive force than the individual elastic elements 17 described above.

According to the invention, the surface 15 of the waist portion facing the user has portions 6a–d of a friction agent in order to increase the friction against the skin and thus prevent the pant diaper from slipping down.

The friction agent can be, for example, a flexible material of hot-melt type, i.e. a fusible glue, which provides a coating with a surface which is smooth and non-porous. It must, however, not stick fast to the skin of the user, even at such high temperatures as 50° C. Flexible in this context means that the material is compliant and thus can follow and be stretched to the same extent as the material in the waist of the pant diaper when it is stretched as the user moves.

A suitable hot-melt material for use in this context is a material based on thermoplastic rubber, for example styrene isoprene rubber (SIS), styrene butadiene rubber (SBR), or styrene ethylene butadiene styrene rubber (SEBS). Other hot-melt materials can also be used, for example within the following groups: ethylene vinyl acetate copolymers, cellulose acetate butyrate, ethyl cellulose, and acrylic materials.

Other examples of friction agents are material of foam-type and water-based materials, for example polyvinyl acetate.

Figure 5:
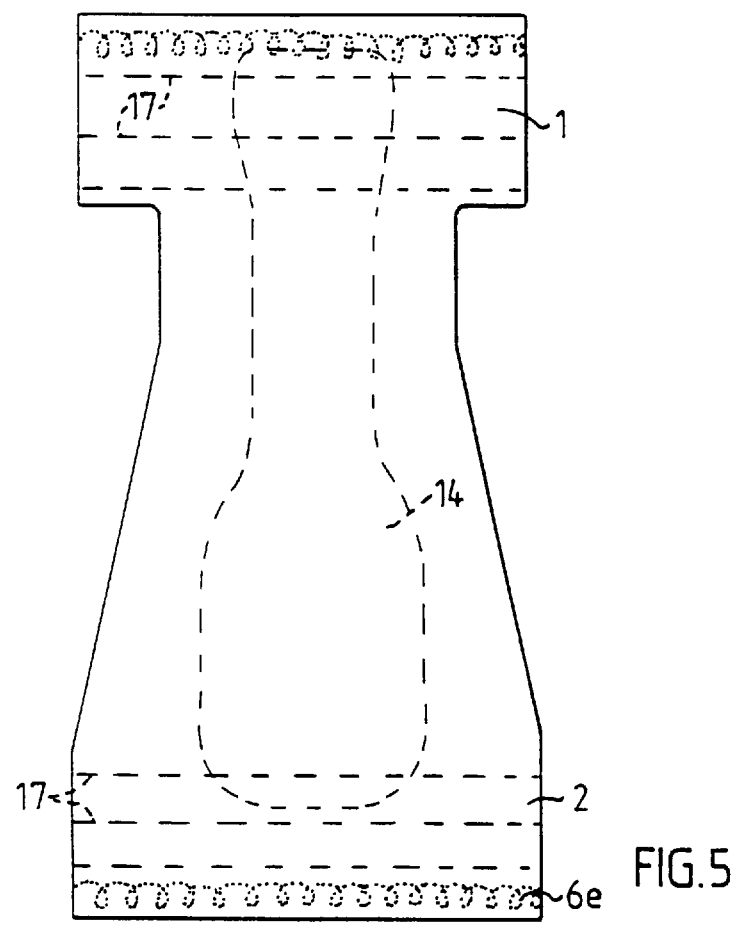
FIG. 5 shows a pant diaper according to the invention with the hot-melt material laid out in a spiral shape.

Portions 6a–d applied at the hip portions but not over the seams between the edge portions 4, 5 and not directly in the centre of the front and back portions have proved to be advantageous since the hands are placed there when pulling the pant diaper on and off. But the elastic hot-melt material can, of course, be applied in a strip or string extending around the entire inside of the waist portion, but this can, however, mean that certain portions of the hot-melt strip will stick to the stomach or backside when the pant diaper is pulled on or off. The hot-melt material can also be applied in the form of drops of glue or in spiral patterns which have been sprayed on various areas around the waist. One example of such an alternative application of hot-melt adhesive is shown in FIG. 5, where the material has been applied by a spray nozzle in a spiral form extending in a strip around the entire waist portion.

It is thus possible with the present invention to make the elastic threads 17 and/or 33 with less tension or fewer number and at the same time achieve the same stay-up capacity with better wearer comfort. In order to achieve the same wearer comfort without the present invention, it would have been necessary to provide pant diapers with many different waist sizes, and this would make the product much more expensive and more difficult to use for the consumer.

Figure 6:
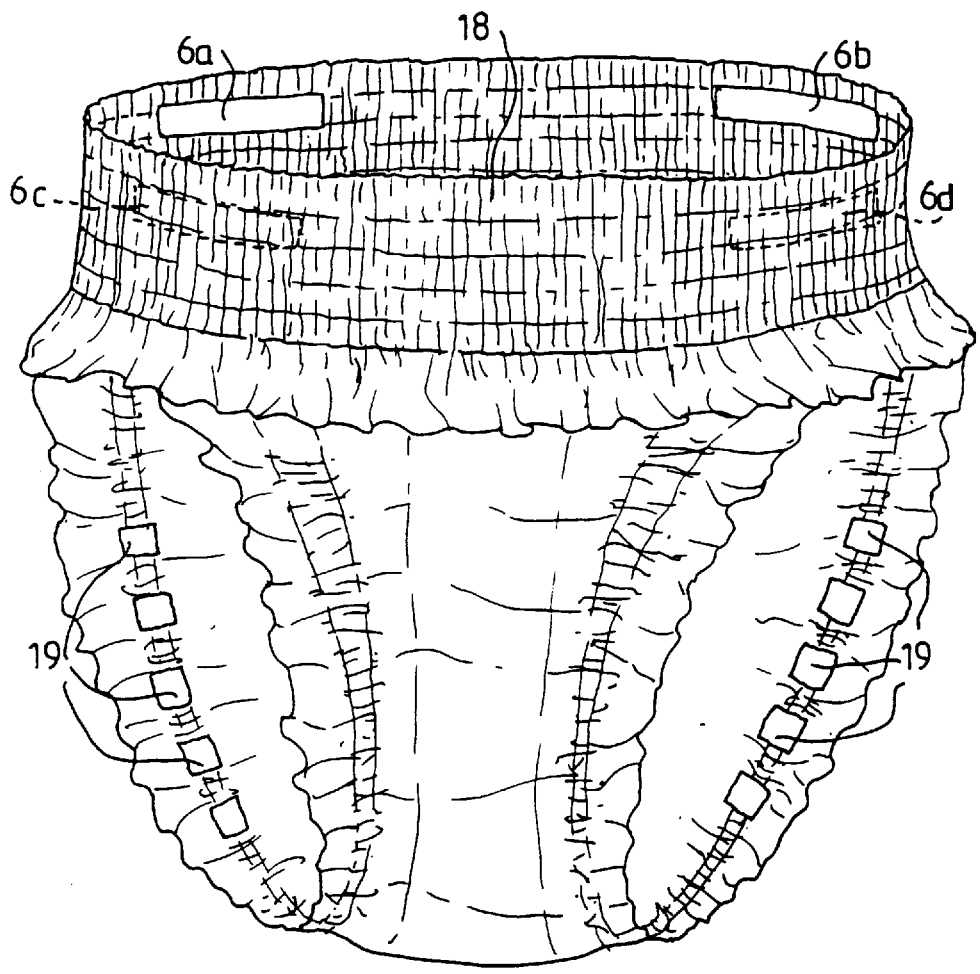
FIG. 6 shows the invention embodied in a pair of disposable menstrual briefs.

FIG. 6 shows the invention embodied in a pair of menstrual briefs where correspondingly labeled strips of hot-melt friction increasing material 6a–d have been applied around the elasticized waist portion of a pair of menstrual briefs to achieve the same advantages as regards comfort and holding up capacity as are achieved in the pant diaper example discussed above.

The menstrual briefs are also provided with friction increasing hot-melt patches 19 along the leg openings facing the buttocks. They prevent the edges of the leg openings in the rear of the briefs from sliding across the buttocks and into the crease between the buttocks, causing discomfort and bunching of the absorbent material.

The invention claimed is:

1. Disposable absorbent pant, comprising a crotch portion, front and back portions adjacent thereto which are joined to form a waist portion of the disposable absorbent pant for surrounding the waist of a user, said waist portion being circumferentially elastic, at least one cover layer extending from at least said front portion to said back portion, an absorbent body disposed adjacent to said at least one cover layer, said absorbent body being held tightly against the body of the user by the elastic waist portion, wherein at least portions of the surface of the waist portion facing the skin of the user are provided with skin engagement means for increasing friction against the skin, relative to the surface of said waist portion, and thereby creating frictional resistance with the skin.

2. Disposable absorbent pant according to claim 1, wherein the friction agent is flexible and compliant with the elastic waist portion.

3. Disposable absorbent pant according to claim 1, wherein the skin engagement means for increasing friction includes a hot-melt material.

4. Disposable absorbent pant according to claim 3, wherein the hot-melt material is based on a thermoplastic rubber.

5. Disposable absorbent pant according to claim 1, wherein the friction agent consists of a water-based material.

6. Disposable absorbent pant according to claim 1, wherein the friction agent consists of a material of foam-type.

7. Disposable absorbent pant according to claim 1, wherein the friction agent is arranged in portions extending in a row around the entire inside of the waist portion.

8. Disposable absorbent pant according to claim 1, wherein the waist portion includes a right hip portion and a left hip portion, the friction agent being arranged in portions which only extend along the right and left hip portions of the waist portion.

9. Disposable absorbent pant according to claim 1, wherein the friction agent extends in a continuous strip along the waist portion.

10. Disposable absorbent pant according to claim 1, wherein the friction agent is arranged in the form of points on the inside of the waist portion.

11. A disposable absorbent diaper comprising:

a crotch portion;

front and back portions adjacent to the crotch portion which are joined together to form a waist portion of the disposable absorbent diaper for surrounding the waist of a user, said waist portion being circumferentially elastic;

at least one cover layer extending from at least said front portion to said back portion; and an absorbent body disposed adjacent to said at least one cover layer, said absorbent body being held tightly against the body of the user by the elastic waist portion;

wherein at least portions of the surface of the waist portion facing the skin of the user are provided with skin engagement means for increasing friction against the skin of the user, relative to the surface of said waist portion, and thereby creating frictional resistance with the skin.

12. Disposable absorbent pant according to claim 1, wherein the absorbent body is connected to said at least one cover layer.

13. Disposable absorbent pant according to claim 1, wherein said at least one cover layer includes two cover layers and the absorbent body is enclosed between the two cover layers.

14. Disposable absorbent diaper according to claim 11, wherein the absorbent body is connected to said at least one cover layer.

15. Disposable absorbent diaper according to claim 11, wherein said at least one cover layer includes two cover layers and the absorbent body is enclosed between the two cover layers.

16. Disposable absorbent pant, comprising a crotch portion, front and back portions adjacent thereto which are joined to form a waist portion for surrounding the waist of a user of the disposable absorbent pant, said waist portion being circumferentially elastic, at least one cover layer extending from at least said front portion to said back portion, an absorbent body disposed adjacent to said at least one cover layer, said absorbent body being held tightly against the body of the user by the elastic waist portion, wherein at least portions of the surface of the waist portion facing the skin of the user are provided with skin engagement means for increasing friction against the skin, relative to the surface of said waist portion, said skin engagement means providing smooth contact surfaces for contacting the skin of the user and creating a frictional resistance therewith.

* * * * *